US008637312B2

(12) United States Patent
Krüger et al.

(10) Patent No.: US 8,637,312 B2
(45) Date of Patent: Jan. 28, 2014

(54) MAMMALIAN CULTURE MEDIA WITH POLYAMINE AND IRON

(75) Inventors: Olaf Krüger, Ulm (DE); Kerstin Oellers, Burgrieden (DE); Lars Kober, Ulm (DE)

(73) Assignee: Cellca GmbH (DE)

( * ) Notice: Subject to any disclaimer, the term of this patent is extended or adjusted under 35 U.S.C. 154(b) by 516 days.

(21) Appl. No.: 12/811,747

(22) PCT Filed: Jan. 7, 2009

(86) PCT No.: PCT/EP2009/000035
§ 371 (c)(1),
(2), (4) Date: Jul. 6, 2010

(87) PCT Pub. No.: WO2009/087087
PCT Pub. Date: Jul. 16, 2009

(65) Prior Publication Data
US 2010/0285533 A1    Nov. 11, 2010

(30) Foreign Application Priority Data

Jan. 9, 2008  (EP) .................................. 08000244

(51) Int. Cl.
*C12N 5/00*    (2006.01)
(52) U.S. Cl.
USPC ............ 435/405; 435/325; 435/366; 435/404
(58) Field of Classification Search
None
See application file for complete search history.

(56) References Cited

U.S. PATENT DOCUMENTS

| 6,048,728 | A | 4/2000 | Inlow et al. |
| 6,184,232 | B1 * | 2/2001 | Bergeron, Jr. ................. 514/316 |
| 2003/0096402 | A1 * | 5/2003 | Lee et al. ...................... 435/325 |
| 2006/0094104 | A1 * | 5/2006 | Grillberger et al. ......... 435/235.1 |

FOREIGN PATENT DOCUMENTS

| EP | 0 481 791 A | 4/1992 |
| WO | WO 98/08934 | 3/1998 |
| WO | WO 01/16294 | 3/2001 |
| WO | WO 02/052025 A | 7/2002 |
| WO | WO 2004/016731 A | 2/2004 |
| WO | WO 2004/078955 | 9/2004 |
| WO | WO 2005/023310 A | 3/2005 |
| WO | WO 2006/045438 A | 5/2006 |
| WO | WO 2006/047380 A | 5/2006 |
| WO | WO 2007/036291 | 4/2007 |
| WO | WO 2007/077217 A | 7/2007 |

OTHER PUBLICATIONS

International Search Report dated Apr. 27, 2009, issued in corresponding international application No. PCT/EP2009/000035.
Katsuta H et al: "Effects of Polyamines on the Proliferation of Mammalian Cells in Tissue Culture" Japanese Journal of Experimental Medicine, Institute of Medical Science, Tokyo, JP, vol. 45, No. 5, Oct. 1975, pp. 345-354, XP009058915 ISSN: 0021-5031.
Gaboriau Francois et al: "Polyamine modulation of iron uptake iri CHO cells" Biochemical Pharmacology, vol. 67, No. 9, May 1, 2004, pp. 1629-1637, XP002477218 ISSN: 0006-2952.
Edwards Chad R et al: "Polyamines as antioxidants in human colon cancer cells (HCTI16) in culture" FASEB Journal vol. 15, No. 4, Mar. 7, 2001, p. A84, XP001538409 & Annual Meeting of the Federation of American Societies for Experimental Biology on Experimental Biol; Orlando, Florida, USA; Mar. 31-Apr. 4, 2001 ISSN: 0892-6638.
Hyvonen T et al: "Monitoring of the Uptake and Metabolism of Aminooxy Analogues of Polyamines in Cultured Cells by High-Performance Liquid Chromatography" Journal of Chromatography. Biomedical Applications, Elsevier, Amsterdam, NL, vol. 574, No. 1, 1992, pp. 17-21, XP009098817 ISSN: 0378-4347.
Valerie G. Brunton, et.al., "Mechanisms of Spermine Toxicity in Baby-Hamster Kidney (BHK) Cells," Biochem. J., 1991, 280, pp. 193-198.
Gail Urlaub, et al., "Isolation of Chinese Hamster Cell Mutants Deficient in Dihydrofolate Reductase Activity," Proc. Natl. Acad. Sci. USA, Jul. 1980, vol. 77, No. 7, pp. 4216-4220.
J.M. Renard, et.al., "Evidence That Monoclonal Antibody Production Kinetics is Related to the Integral of the Viable Cells Curve in Batch Systems," Biotechnology Letters, 1988, vol. 10, No. 2, pp. 91-96.
Diana A. Averill-Bates, et.al., "Cytotoxicity and Kinetic Analysis of Purified Bovine Serum Amine Oxidase in the Presence of Spermine in Chinese Hamster Ovary Cells," Archives of Biochemistry and Biophysics, Jan. 1993, vol. 300, No. 1, pp. 75-79.
Hiroyuki Itoh, et.al., "Iron Ion Induces Mitochondrial DNA Damage in HTC Rat Hepatoma Cell Culture—Role of Antioxidants in Mitochondrial DNA Protection from Oxidative Stresses," Archive of Biochemistry and Biophysics, Aug. 15, 1994, vol. 313, No. 1, pp. 120-125.

* cited by examiner

*Primary Examiner* — Blaine Lankford
(74) *Attorney, Agent, or Firm* — Ostrolenk Faber LLP (57) ABSTRACT

The present invention relates to an improved cell culture additive with a content of polyamines and iron, media containing it and processes for using it for an improved cell growth, cell viability or cellular productivity.

15 Claims, 9 Drawing Sheets

MAMMALIAN CULTURE MEDIA WITH POLYAMINE AND IRON

CROSS REFERENCE TO RELATED APPLICATIONS

The present application is a 35 U.S.C. §§371 national phase conversion of PCT/EP2009/000035, filed Jan. 7, 2009, which claims priority of European Patent Application No. 08000244.7, filed Jan. 9, 2008, the disclosure of which is incorporated herein by reference. The PCT International Application was published in the English language.

TECHNICAL FIELD

The present invention relates to an improved cell culture additive with a content of polyamines and iron, media containing it and processes for using it for an improved cell growth, cell viability or cellular productivity.

BACKGROUND

Cell culture process development aims inter alia to increase the integral of viable cell concentration (IVC) and to increase cellular product formation. IVC correlates directly with product concentration (Renard, J. M., et. al., Biotechnology Letters, 1988, 10(2): 91-96). The IVC can be increased by increased peak viable cell concentration or by prolonged culture duration. The process time can be prolonged, if cell viability remains high, e.g. if the stationary growth phase can be prolonged. A good cell culture medium or a good cell culture process would supply the cells with all necessary substrates during the whole process, resulting in good cell growth, viability or product formation.

Polyamines, for example spermidine or spermine, are ubiquitous cell components essential for cell growth and productivity. Despite this, spermine is reported to be toxic to adherent growing BHK (baby hamster kidney) cells in a serum containing medium (Brunton, V. G. et. al., Biochem. J., 1991, 280: 193-198). Bovine serum albumin fraction accelerates the cytotoxicity of polyamine, especially of spermine (Katsuta, H., Jpn J Exp Med., 1975, 45(5): 345-54). The treatment of CHO (Chinese hamster ovary) cells with 10 µM ferric iron (1.6 mg/l) plus increasing concentrations of spermine (0 to 100 µM, maximum 20.2 mg/l) decreases the number of viable cells in a dose-dependent manner in a serum containing medium (Gaboriau, F., et. al., Biochemical Pharmacology, 2004, 67: 1629-1637). Bovine serum contains the enzyme bovine serum amine oxidase, which catalyzes the oxidative deamination of polyamines. WO 98/08934 discloses a serum free medium containing 0.9 to 18.1 mg/l spermine, in particular 9.05 mg/l. The formed oxidation products of polyamines are responsible for cytotoxicity (Averill-Bates, et. al., Arch Biochem Biophys., 1993, 300(1): 75-9). The oxidative products of polyamines may also act as negative regulators of cell growth.

In summary, published data demonstrates that even though polyamines are essential for cells, they are toxic to mammalian cells. Thus, a skilled person was focussed in optimising the putrescine (a diamine) and not the polyamine concentration in cell culture media. Putrescine is the precursor of polyamines. Some examples of putrescine containing media are described in WO 2004/078955.

An oligopeptide-free medium comprising at least 0.5 mg/l of a polyamine is shown to promote cell specific productivity in WO 2007/077217. It is further demonstrated, that the most efficient amine is putrescine. Increasing the spermine concentration above 2 mg/l does not significantly increase the cellular productivity. The document also discloses the supplementation of the medium with 1,067 mg/l additional Fe (II). No synergistic effect of the polyamine and iron is seen.

WO 98/08934 discloses a spermine-containing medium containing $Fe^{2+}$ and/or $Fe^{3+}$ from 0.28 mg/l to 1.1 mg/l.

Thus, there still remains a need for the provision of culture media and additives to supplement them which provide an improved cell growth, cell viability and cellular productivity.

SUMMARY

The technical problem underlying the present invention is to provide cell culture media, components and uses thereof, which overcome the above-identified disadvantages, in particular enable cell culture processes within an increased IVC and/or increased cellular product formation.

The present invention solves the above-identified problem by the provision of the teachings of the independent claims. In particular, the present invention provides a cell culture additive containing at least one polyamine at a concentration of at least, preferably higher than, 20 mg/l and at least one iron source at a concentration of at least, preferably higher than, 2 mg/l.

We have surprisingly found that a polyamine concentration in culture media significantly higher than usual is not toxic for cells, but instead promotes cell growth, cell viability and/or cellular productivity. Without being bound by theory and in a non-binding way we believe that if cells are provided with a diamine such as putrescine in culture media, they synthetise cellular polyamines, like spermine, from putrescine using cellular energy. In addition, said cellular polyamine synthesis probably requires a considerable time to build up a sufficiently great internal polyamine pool for a rapid cell growth. If on the other hand the polyamine concentration in the cell culture media is increased, the cell metabolism does not have the need to synthesise polyamines and saves cellular energy for growth and productivity.

Although it is known that oxidative products of iron are toxic to cells which are specifically formed at high iron concentrations and/or at long process time and although it is known that the mitochondrial DNA of rat hepatoma cells is damaged in the presence of either 100 µM of ferrous ($Fe^{2+}$) or ferric ($Fe^{3+}$) iron in culture medium (Itoh, H. et. al., Arch Biochem Biophys., 1994, 313: 120-125), the present invention applies high iron concentrations in the present polyamine containing additives and media containing them. The high iron concentration surprisingly promotes cell growth in the presence of polyamines in culture media. Due to their amino groups, polyamines are obviously able to chelate metallic cations. The stability constants of these chelates increase with the number of amino groups and with the chain length of the polyamines. Thus, without being bound by theory and in a non limiting way, we believe that polyamines play a protective role against iron oxidation through chelate formation. We believe that polyamines bind the iron ions, stabilise the oxidative status of the iron and assist in transporting iron into the cells. Polyamines might also act as chelator preventing precipitation of $Fe^{2+}/Fe^{3+}$ ions.

The presently used high concentrations of a polyamine in combination with an iron source promote cell growth, cell viability or cellular productivity. According to our finding the polyamines are not only a substrate but also may act as a carrier of positively charged ions, like transition metals, for example $Fe^{2+}$, $Fe^{3+}$, $Cu^{2+}$, $Zn^{2+}$ in media. For the efficient formation of polyamine-iron complexes higher polyamine and iron concentrations are beneficial. Said formed polyamine-iron complexes are easily taken up by cells and ensure better cellular iron and polyamine supply resulting in higher cell growth, cell viability and/or cellular productivity. Therefore, polyamine and iron concentrations should be increased to the present concentration in the culture media according to the present invention.

Supplying cells with polyamines and the iron source according to the present invention is in particular useful for high cell density production processes or production processes with prolonged process time, like in fed-batch process or perfusion process. With an increased process duration it becomes important to add a polyamine and an iron source into the culture to avoid their limitation. Since both substances, polyamine and iron source, may be sensible against oxidation and since it is important therefore to protect them against oxidation and to increase their concentration corresponding to the high cell density, the presently provided teaching to supply both substances together with high concentrations so as to provide polyamine-iron complex formation is very useful.

In particular, the present invention solves the above-identified problem by the provision of said culture additives, in particular culture medium additives, and further by the provision of culture media, which comprise said culture additives, which are defined by a particular combination of a high polyamine, in particular spermine or spermidine, and high iron source concentration.

DETAILED DESCRIPTION

The present invention therefore relates in a particularly preferred embodiment to culture additives according to the above, wherein the polyamine is contained therein in a concentration of at least, preferably more than, 25, at least, preferably more than, 30, at least, preferably more than, 35, at least, preferably more than, 40, at least, preferably more than, 45, or in a particularly preferred embodiment at least, preferably more than, 50 mg/l. In a furthermore preferred embodiment, the present invention provides a culture additive according to the above, wherein the concentration of the iron source is at least, preferably more than, 5, at least, preferably more than, 10, at least, preferably more than, 15, at least, preferably more than, 50, at least, preferably more than, 100, at least, preferably more than, 240, or in a particularly preferred embodiment at least, preferably more than, 480 mg/l.

In a furthermore preferred embodiment of the present invention, the culture medium of the present invention is a culture medium, wherein the concentration of the polyamine is from 30 to 120 mg/l, in particular from 40 to 120 mg/l. In a particularly preferred embodiment, the culture medium has a concentration of the iron source from 50 to 900 mg/l, preferably from 50 to 450 mg/l. In a furthermore preferred embodiment of the present invention, the culture medium has a concentration of the polyamine from 30 to 120 mg/l and the concentration of the iron source is from 50 to 900 mg/l, in particular 50 to 450 mg/l. All concentration values given herein for the iron source relate to the mass of the entire iron source, and not only the iron itself, if not otherwise stated.

In the context of the present invention, a culture additive is meant to become a component of a culture medium and can in one embodiment be added in a quantity to a conventional state of the art culture medium, so as to provide a culture medium of the present invention with the required concentrations of the at least one polyamine and the at least one iron source in accordance with the present invention. Of course it is also possible to prepare a culture medium of the present invention by adding various components to a culture additive of the present invention, thereby forming a culture medium of the present invention. In one preferred embodiment the culture additive comprises the polyamine and the iron source in a 2 to 10000 times, preferably 10 to 1000 times, in particular in a 100 times, higher concentration as identified above for the culture medium, i.e. the culture additive has a concentration of the polyamine from 60 to 1200000 mg/l and the concentration of the iron source is from 100 to 9000000 mg/l, in particular 100 to 4500000 mg/l. In a furthermore preferred embodiment, the culture additive has a concentration of the polyamine from 300 to 120000 mg/l and the concentration of the iron source is from 500 to 900000 mg/l, in particular 500 to 450000 mg/l. In a furthermore preferred embodiment, the culture additive has a concentration of the polyamine from 4000 to 12000 mg/l and the concentration of the iron source is from 5000 to 90000 mg/l, in particular 5000 to 45000 mg/l. In a particularly preferred embodiment, the culture media of the present invention contain the culture additive of the present invention in an amount such as to provide a concentration of the at least one polyamine of at least 20, 25, 30, 35, 45 or particularly 50 mg/l and a concentration of the at least one iron source of at least 2, 5, 10, 15, 50, 100, 240 and at least 480 mg/l in the culture medium. In a particularly preferred embodiment, the culture media of the present invention comprise the culture additive of the present invention in an amount such as to provide a concentration of the at least one polyamine from 30 to 120 mg/l and a concentration of the at least one iron source from 50 to 900 mg/l, preferably 50 to 450 mg/l.

In a furthermore preferred embodiment, the culture additive of the present invention is a culture medium additive. In a furthermore preferred embodiment, the culture medium is a cell culture medium. In a furthermore preferred embodiment, the culture medium is a feeding medium.

The following terms are synonymous and mean the same: "culture medium" and "cell culture medium". A "culture medium" is a medium which is suitable for cultivation or for incubation of a cell. Such culture media may contain nutrients for keeping the cell integrity or cell viability or cell growth or cellular productivity. Preferred as a culture medium is a liquid culture medium. A particularly preferred culture medium is described in WO 2007/036291 and may be used for the present invention. A basal medium is a particular embodiment of a culture medium and may preferably be combined with other components, for example with a feed medium. A particularly preferred basal medium contains all necessary substances for cell growth, cell viability and cellular productivity. A preferred basal medium in particular may contain for example and not being limited glucose at 1.0-6.0 g/l, NaCl 2.8-6.2 g/l, KCl 273-945 mg/l, CaCl$_2$ 48-290 mg/l, MgCl$_2$ 42-330 mg/l, NaH$_2$PO$_4$ 56-1130 mg/l, Arginine 56-930 mg/l, Asparagine 44-900 mg/l, Aspartic acid 26-445 mg/l, Cysteine 35-270 mg/l, Glutamic acid 44-900 mg/, Glutamine 44-900 mg/l, Glycine 18-180 mg/l, Histidine 42-670 mg/l, Isoleucine 54-877 mg/l, Leucine 59-1250 mg/l, Lysine 73-1120 mg/l, Methionine 9-454 mg/l, Phenylalanine 35-677 mg/l, Proline 17-828 mg/l, Serine 26-1339 mg/l, Threonine 24-989 mg/l, Tryptophane 9-441 mg/l, Tyrosine 55-565 mg/l, Valine 52-787 mg/l, NaHCO3 2,4 g/l. A preferred basal medium may further comprise fatty acids and nucleotides.

The following terms are synonymous: "feed medium", "feeding medium" and "perfusion medium". The "feed medium" is a particular embodiment of a culture medium, which is added into a cell culture during the cultivation process. In other words, a feed medium is a medium, which is added to a cell culture after contacting the cells with a first medium, e.g. basal medium. Addition of a feed medium into a culture has several purposes, for example it can prolong culture longevity, can increase cell viability, can increase cell concentration, or can increase product concentration. A particularly preferred feed medium is described in WO 2007/036291 and may be used for the present invention. A preferred feed medium of the present invention contains all necessary substances for cell growth, cell viability and cellular productivity. A feed medium, for example, and not being limited to salts, preferably contains trace elements, carbohydrates, amino acids, fatty acids, pH regulator and nucleotides. Feed media consisting of only one or more of above mentioned substances are also suitable.

According to the invention the present polyamine and iron concentrations, i.e. the present culture additives can in a preferred embodiment be used in a culture medium, a basal medium or in a feed medium. Thus, in the context of the invention, a culture or cell culture medium containing a culture additive is meant to be a culture medium, a basal or feed medium as explained above, which contains the culture additive.

A culture additive may in a particularly preferred embodiment contain in addition to the at least one polyamine and the at least one iron source at least one solvent, such as water or an aqueous salt solution. Thus, a culture additive may in a preferred embodiment be in liquid form.

A culture medium to which a culture additive of the present invention is added, may be a conventional culture medium. A culture medium of the present invention may contain other components besides the culture additives of the present invention, such as solvents, for instance water, vitamins, salts, carbon sources and/or nitrogen sources, amino acids, pH regulators, trace elements, fatty acids, nucleotides. In particular, the culture medium of the present invention is an aqueous medium.

The cell culture of mammalian cells is nowadays a routine operation well-described in scientific textbooks and manuals. It is covered in detail e.g. in R. Ian Fresney, Culture of Animal cells, a manual, 4th edition, Wiley-Liss/N.Y., 2000. Culture media and culture methods, for instance for mammalian cell lines, for use in combination with the culture additives of the present invention are per se well-known in the art. Such culture media are preferably composed of a solvent, such as water, a carbon source, a nitrogen source, amino acids, pH regulators, trace elements, fatty acids, nucleotides. Preferred culture media for the present invention are standard cell culture media, which may also be adapted to the needs of particular cell types and include, without being restricted to, Roswell Park Memorial Institute (RPMI) 1640 medium, L-15 medium, Dulbecco's modified Eagle's medium (DMEM), Eagle's minimal essential medium (MEM), Ham's F12 medium or Iscoves' modified DMEM. Other preferred media are for instance, Ham's F10 or F12 media, which are specially designed for CHO cell culture. Other preferred media for the present invention are specially adapted to CHO cell culture and are described for instance in EP 0 481 791. A preferred culture medium for the present invention can also be a commercially available medium, for example, but not limited to CD CHO (Gibco, 10743), ProCHO5 (BioWhittaker, BE12-766Q), HyQSFM4CHO (HyClone, SH30548.02).

The cell culture media of the present invention may in a preferred embodiment of the present invention contain proteins. These proteins can be produced either recombinantly or are isolated from a natural source, for example transferrin, insulin or bovine serum albumine. The protein is preferred recombinantly produced, for example recombinant insulin or recombinant bovine serum albumine or recombinant human serum albumine.

In a particularly preferred embodiment of the present invention, the culture additives and/or the culture media of the present invention are protein-free.

In a further preferred embodiment of the present invention, the culture additives and/or the culture media of the present invention are glutamine-free.

In a particularly preferred embodiment of the present invention, the culture additives and/or the culture media of the present invention are free of animal components.

Preferred culture media of the present invention may in one embodiment also contain hydolysates from animal source, from plant source or from yeast. Preferred is a hydrolysate from plant source, e.g. soy bean peptone or yeast hydrolysate. Culture media of the present invention can in one embodiment contain peptides. The peptide may be a dipeptide, a tripeptide, an oligo- or polypeptide.

In a particular preferred embodiment, the culture additives and/or culture media of the present invention are serum-free. In a particular preferred embodiment, the culture additives and/or culture media of the present invention are protein-free. In a particular preferred embodiment, the culture additives and/or culture media of the present invention are free of products isolated from animals. In a particularly preferred embodiment of the present invention, the culture additive and/or culture medium are free of hydrolysates. In a furthermore preferred embodiment, the culture additive and/or culture media are free of peptides.

The present culture additives or the culture media contain in a preferred embodiment one or more other cellular nutrients, i.e. a carbon source, e.g. glucose, and a nitrogen source, e.g. amino acids, and/or salts. According to the invention the present culture additives may in a preferred embodiment be in the form of one or more stock solutions, for instance one iron source containing stock solution and one polyamine containing stock solution. In another preferred embodiment, the stock solution contains both, namely the at least one polyamine and the at least one iron source. The polyamine and/or iron source may preferably be highly concentrated in said stock solutions. The stock solutions may contain additional components, such as salts or pH regulators. Such stock solutions can be used by being added into a culture medium to form a culture medium of the present invention or into a feed medium or into a cell culture. A stock solution is also defined herein as a "kit". Through the addition of the kit, the desired concentration of polyamine and iron is adjusted in the final medium or in the cell culture.

The culture medium or culture additive may also comprise additional substances, in particular aurin tricarboxylic acid (ATA), dichloro acetic acid (DCA) and/or succinic acid. Of course, one or more of the acids may be present in form of salts thereof and derivatives thereof. According to the invention, the polyamine and the iron source can be combined in a preferred embodiment of the culture additive or culture medium of the present invention with dichloro acetic acid, or salts thereof or derivatives thereof, such as dichloroacetate (DCA) or salts thereof, for example sodium dichloro acetate.

According to the invention the polyamine and the iron source can be combined in a preferred embodiment of the culture additive or culture medium of the present invention with succinic acid or salts thereof, for example sodium succinate dibasic hexahydrate.

According to the invention, the polyamine and iron can be combined in a preferred embodiment of the culture additive or culture medium of the present invention with aurin tricarboxylic acid (ATA) or salts thereof.

In a particularly preferred embodiment the culture medium or culture additive comprises spermine, iron citrate, sodium dichloro acetate, sodium succinate dibasic hexahydrate and aurin tricarboxylic acid.

In a particularly preferred embodiment a culture additive of the present invention comprises 100 to 900, preferably 400 mg/l polyamine, in particular spermine, 1 to 10, preferably 4 g/l iron source, in particular iron citrate and optionally one or more of the following: 5 to 100, preferably 20 mM sodium dichloro acetate, 5 to 100, preferably 30 g/l sodium succinate dibasic hexahydrate and 5 to 100, preferably 25 mg/l aurin tricarboxylic acid.

The term "polyamine" is meant to identify organic compounds, composed of carbon, nitrogen, and hydrogen and containing two or more amino groups. Examples of particularly preferred polyamines for use in the present invention are spermine, spermidine, norspermine, norspermidine, homospermine, homospermidine, cadaverine, putrescine, agmatine and ornithine. The hydrated or dehydrated forms, various salt forms or combination of one or more of polyamines are all comprised in the term polyamines.

The term "iron" is meant to identify the transition metal Fe with atomic weight of 55,845. The term iron is the generic term which comprises all molecules containing one or more iron ions for example $Fe^{3+}$ and/or $Fe^{2+}$ ions. The $Fe^{3+}$ and/or $Fe^{2+}$ ion can occur in form of an iron salt. Iron salts can be hydrated or dehydrated. In a particularly preferred embodiment, the iron source contains Fe (II) and/or Fe (III) ions. In a particularly preferred embodiment, the iron source for use in the present invention is selected from the group consisting of iron (III) phosphate, iron (III) pyrophosphate, iron (III) nitrate, iron (II) sulphate, iron (III) chloride, iron (II) lactate, iron (III) citrate, ammonium iron (III) citrate, iron-dextran and ethylenediaminetetraacetic acid ferric sodium salt or hydrated or dehydrated forms thereof.

The iron can also be complexed with another molecule, e.g. with a carrier or with a chelator. Some particularly preferred examples of complexed iron with chelators are iron (II) lactate hydrate, iron (III) citrate (CAS number: 3522-50-7), ammonium iron (III) citrate, iron-dextran and ethylenediaminetetraacetic acid ferric sodium salt (CAS number: 15708-41-5).

The iron may also be complexed with the following additional molecules such as described in U.S. Pat. No. 6,048,728, i.e. pyridoxyl isonicotinoyl hydrazone, citrate, choline citrate, acetylacetonate, and a variety of other organic acids such as malic acid, succinic acid, fumaric acid, and alpha ketoglutaric acid. Further iron chelators for use in the present invention are given in WO 2001/016294.

Some particularly preferred examples of iron for use in the present invention are iron (III) phosphate, iron (III) pyrophosphate hydrate, iron dextran, iron (III) nitrate nonahydrate, iron (II) sulphate heptahydrate, iron (III) chloride hexahydrate, iron (III) citrate, ammonium iron (III) citrate.

The present invention also relates to a process for preparing a culture medium, wherein a culture additive according to the present invention is added to a liquid medium, in particular to a conventional state of the art culture medium.

The present invention also relates to the use of a culture additive according to the present invention to prepare a culture medium.

A further aspect of the present invention is a process, in which cells are contacted with a culture medium which contains at least one polyamine at a concentration of at least, preferably higher than, 20 mg/l and at least one iron source at a concentration of at least, preferably higher than, 2 mg/l. Culturing cells with a medium according to the present invention comprises in a preferred embodiment of the present invention also a gradual increase of the concentration of either polyamine or iron or both, for instance in a culture vessel, so that the preferred final concentration of these components results during the cell cultivation process. Increasing the concentration of one or both substances may, in a preferred embodiment, also be conducted by adding the polyamine and/or iron source to the culture medium or into the cell culture from one or more stock solutions.

The present invention also relates to a process for culturing cells in a culture medium, wherein a) the cells and a first culture medium are provided and b) the cells are cultivated in said first culture medium under conditions appropriate for maintenance of said cells and said first culture medium and c) wherein at least one polyamine source or at least one iron source or both are added to the first culture medium before inoculating said first culture medium with cells or after inoculating said first culture medium with cells or during the cultivation, so that the sum of all polyamines present and added in steps a), b) and c) and the sum of all iron sources present and added in steps a), b) and c) result in a concentration according to the present invention, in particular results in a concentration of the at least one polyamine of at least 20 mg/l and a concentration of the at least one iron source of at least 2 mg/l.

Thus, the present invention envisages such a process for culturing cells in a culture medium, which foresees that the sum of all polyamines present in the culture medium including polyamines which were added during the cultivation and possibly including polyamines, which have already been consumed and the sum of all iron sources present in the culture medium including iron sources, which were added during the cultivation and possibly including iron sources, which have already been consumed result in a theoretical concentration according to the present invention, that means wherein such a theoretical concentration of the sum of the at least one polyamine is at least 20 mg/l and of the sum of the at least one iron source is at least 2 mg/l.

According to the present invention all known cell culture process embodiments are suitable for being applied in the present invention. A preferred process embodiment of the present invention is a high cell density process. A high cell density process is defined as a process in which the cell concentration exceeds $1\times10^5$/ml, preferred $1\times10^6$/ml, most preferred $1\times10^7$/ml.

According to the present invention, preferred embodiments are continuous processes, batch processes, split-batch processes, fed-batch processes or perfusion processes. In a particularly preferred embodiment, the process for culturing cells is a fed-batch-process. The details of the process embodiments are well known to the skilled person. More detailed definitions of the process embodiments are described in WO 2007/036291. As a non-binding example, a typical fed-batch process starts with inoculation of culture medium with cells. After contacting the cells with a culture medium, the cell culture will be contacted with another medium, for example a feed medium. Contacting cells with a feed medium (feeding) can be but is not limited to 1 to 4 days after inoculation. Addition of the feed medium into the cell culture can be continuous, in intervals or batch wise. The culture volume can increase through the addition of feed medium into the culture.

According to the invention preferred are processes with a long culture duration. A long culture duration is defined as a process time of the production step (n step) which is at least 4 days or longer, preferred at least 8 days or longer, more preferred at least 10 days or longer, more preferred at least 12 days or longer, most preferred at least 14 days or longer.

The present invention is not limited to any type of cells. Examples of cell types include mammalian cells, insect cells, bacterial cells, and yeast cells. The cells can also be primary cells or stem cells. The cells may be naturally occurring cells being not transformed or transfected. The cells can also be recombinant cells transfected of transformed with one or more vectors for recombinant gene expression. The cells can be transformed with a virus for producing any product, for example viral products. The cells can originate from hamster, mouse, human or any other animal. The cells can also be cell lines, for example but not limited to CHO cells, NS0 cells, Per.C6 cells, BHK cells, SP2/0 cells.

The present invention therefore also relates to a process for culturing cells in a culture medium, wherein a) the cells and the culture medium according to the present invention are provided and b) the cells are cultivated in said culture medium under conditions appropriate and suitable for maintenance, that means for cultivating said cells in said culture, in particular for providing conditions for growth and/or amplification of the cells and/or for production of products of these cells. In a particularly preferred embodiment, the cells are cultivated in said medium for more than two passages or more than 4 days. In a furthermore preferred embodiment, the process for culturing cells in the culture medium is a process, which is a production process for a cellular product, in particular a protein expressed, in particular expressed and secreted from the cell.

In a furthermore preferred embodiment, the present invention relates to a process for culturing cells in a culture medium, wherein a) the cells and a first culture medium, in particular a conventional culture medium are provided and b) the cells are cultivated in said first culture medium under conditions appropriate for maintenance of said cells in said culture and wherein at least one culture additive according to the present invention is added a) before inoculating the culture medium with cells and/or b) after inoculating the culture medium with cells and/or c) during the cultivation and/or d) at the beginning and during cultivation so as to provide a second culture medium, which is a culture medium of the present invention in a successively prepared manner, that means by gradually increasing the polyamine and/or iron source concentrations to the high concentrations of the present invention.

Further preferred embodiments of the present invention are the subject-matter of the sub-claims.

The following examples and the accompanying figures describe the present invention in more detail.

EXAMPLES

The following examples are provided only for the purpose of illustrating the invention. They should not, therefore, be construed as limiting the invention in any way.

Materials and Methods

Cells

For all experiments a CHO DG44 host cell line (Urlaub and Chasin, Proc. Natl. Acad. Sci. USA, 1980, 77: 4216) was used. This host cell line was transfected with a vector carrying the gene of an IgG antibody. Transfectants were amplified using MTX in culture medium. An antibody producing clone was isolated and this clone was then used for all experiments.

Cell Culture Conditions

Stock culture cells were kept in a shake flask or in a spinner flask. The stock culture was split into fresh culture medium every two or three days. That means, a small amount of cell culture was used as inoculum and transferred into a new flask and supplemented with fresh culture medium. Cells were cultured at 37° C. in $CO_2$ atmosphere in an incubator. In this way cells were cultured in several passages. One passage is defined as a culture duration of 2-4 days. At different time points inoculum cells were taken from the stock culture and experiments were performed in various scales, for examples in 6-well plates, shake flasks, T-flasks, spinner flasks and bioreactors.

Culture Media

A basal medium as follows (in the following also termed proprietary culture medium) was used for cultivation of cells in all steps, e.g. in the stock culture, in the culture expansion step and in the production step. The basal medium contains all necessary substances for cell growth, cell viability and cellular productivity. The basal medium contains glucose at 1.0-6.0 g/l, NaCl 2.8-6.2 g/l, KCl 273-945 mg/l, $CaCl_2$ 48-290 mg/l, $MgCl_2$ 42-330 mg/l, $NaH_2PO_4$ 56-1130 mg/l, Arginine 56-930 mg/l, Asparagine 44-900 mg/l, Aspartic acid 26-445 mg/l, Cysteine 35-270 mg/l, Glutamic acid 44-900 mg/, Glutamine 44-900 mg/l, Glycine 18-180 mg/l, Histidine 42-670 mg/l, Isoleucine 54-877 mg/l, Leucine 59-1250 mg/l, Lysine 73-1120 mg/l, Methionine 9-454 mg/l, Phenylalanine 35-677 mg/l, Proline 17-828 mg/l, Serine 26-1339 mg/l, Threonine 24-989 mg/l, Tryptophane 9-441 mg/l, Tyrosine 55-565 mg/l, Valine 52-787 mg/l, NaHCO3 2,4 g/l. The basal medium further comprises fatty acids and nucleotides. In all batch and fed-batch experiments the same proprietary culture medium and proprietary feed medium were used, unless otherwise stated. The feed medium used in fed-batch experiments (in the following also termed "proprietary feed medium") has all necessary substances for cell growth, cell viability and cellular productivity, in particular salts, trace elements, carbohydrates, amino acids, fatty acids, pH regulator, nucleotides. Even though here a rich feed medium is used containing above mentioned substances, feed media must not comprise all of these components. Feed media consisting of one or more of above mentioned substances are suitable also. Both basal medium and feed medium are serum free, protein free, peptone free and peptide free. However, supplementation of media with one or more of above mentioned additives is possible. Thus, both media are chemically defined, consisting of only single, fully defined chemicals.

Experiments were performed either in batch or in fed-batch modus. If an experiment was designed for fed-batch modus, it was started by inoculating the flask with stock culture cells in the production medium (culture medium). Culture flasks were inoculated with an inoculation cell density of 2 to $4\times10^5$ viable cells per millilitre. Cells were cultured for 1 to 4 days. The culture was supplemented thereafter with a feed medium for first time. Feeding was done batch wise every 1 to 3 days. Feeding the culture with feed medium was performed batch wise (bolus addition). Feeding of culture can also be done continuously, especially in bioreactors. In fed-batch experiments two different feed media were used. However, it is possible to use one or more than two different feed media. The culture was incubated as long as the cell viability was greater than 50%. Thus, culture duration was approximately 10 to 18 days. Every day samples were taken from cultures and analytical processes were done, such as cell count and metabolite measurements. The antibody concentration was determined in the supernatant of the cell culture using ELISA or protein A HPLC.

The stock solutions were prepared from test substances and the basal media and/or feed media were supplemented in order to achieve their final concentration. Unless otherwise stated, all chemicals are obtained from Sigma (St. Louise, Mo.). In the present examples, the Sigma catalogue number of the chemicals is given. The stock culture cells were centrifuged before inoculating the production flask containing the test substances. The cell pellet was resuspended in the corresponding media. In this way the carry-over effect of substances through inoculum culture was avoided. However, under real production conditions the centrifugation of the inoculum culture is not required and will not be done.

Example 1

Test of Polyamine and Iron Separately and in Combination

Figure 1:
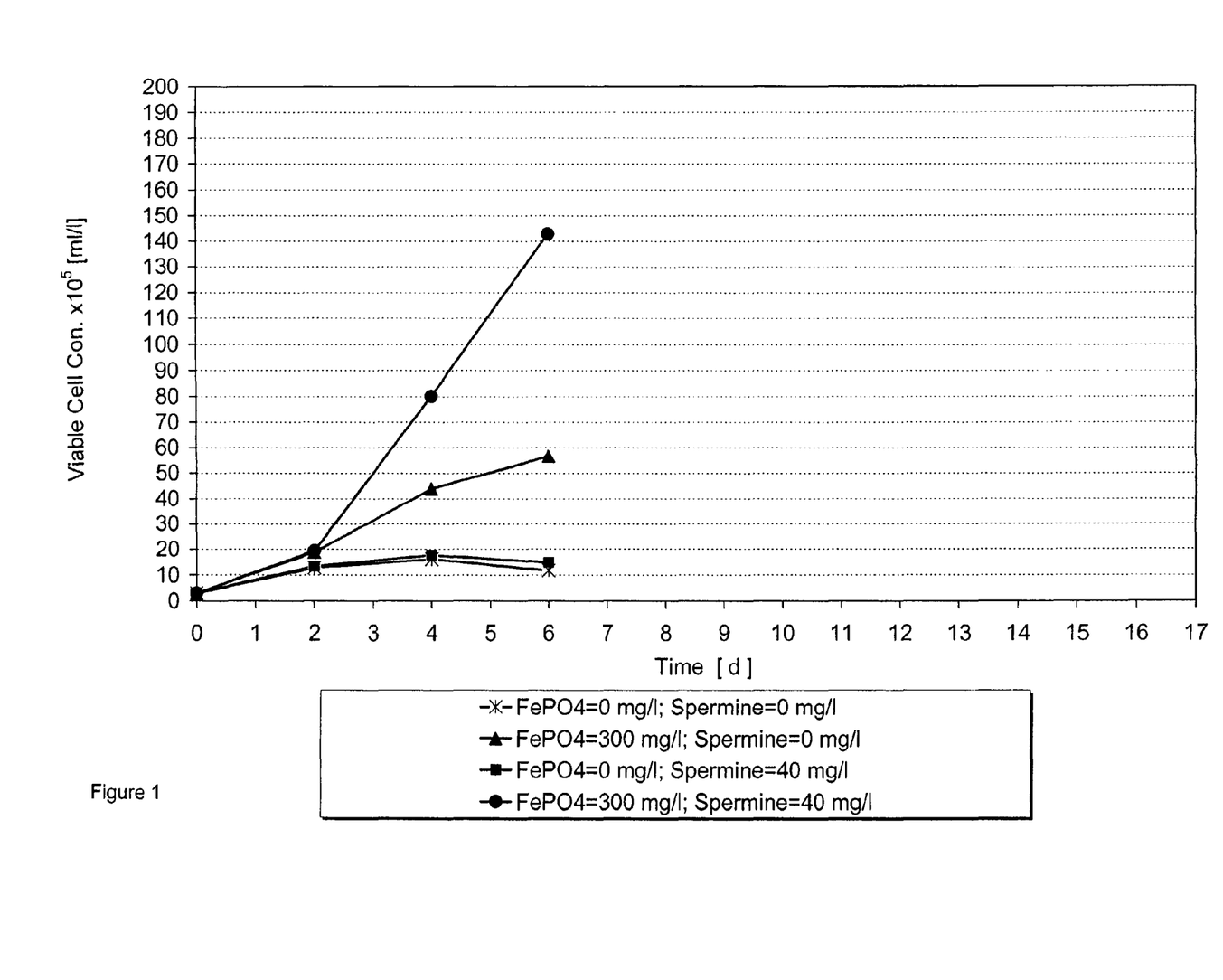
FIG. 1 demonstrates the synergistic effect of polyamines and iron in a high cell density fed-batch process.

This example demonstrates the synergistic effect of a combination of high concentrations of polyamine and iron. A cell culture medium is prepared without iron source and without (w/o) polyamine source. Corresponding amounts of stock solutions are pipetted into the culture medium to adjust the final concentration of test substances (i.e. polyamine and iron source). Then the so prepared culture media are inoculated with cells. The experiment is performed in fed-batch modus. The feed media used are polyamine and iron free. FIG. 1 demonstrates that iron is essential for cell growth. Most importantly, cell growth is stimulated if both spermine and iron are available at the same time at high concentration. To our surprise, both substances display a synergistic effect for cell growth.

Example 2

Test of Spermidine as Polyamine Source at a High Concentration in a Batch Process (SF40)

The aim was to demonstrate that spermidine has a similarly positive effect to spermine on cell growth.

Figure 2:
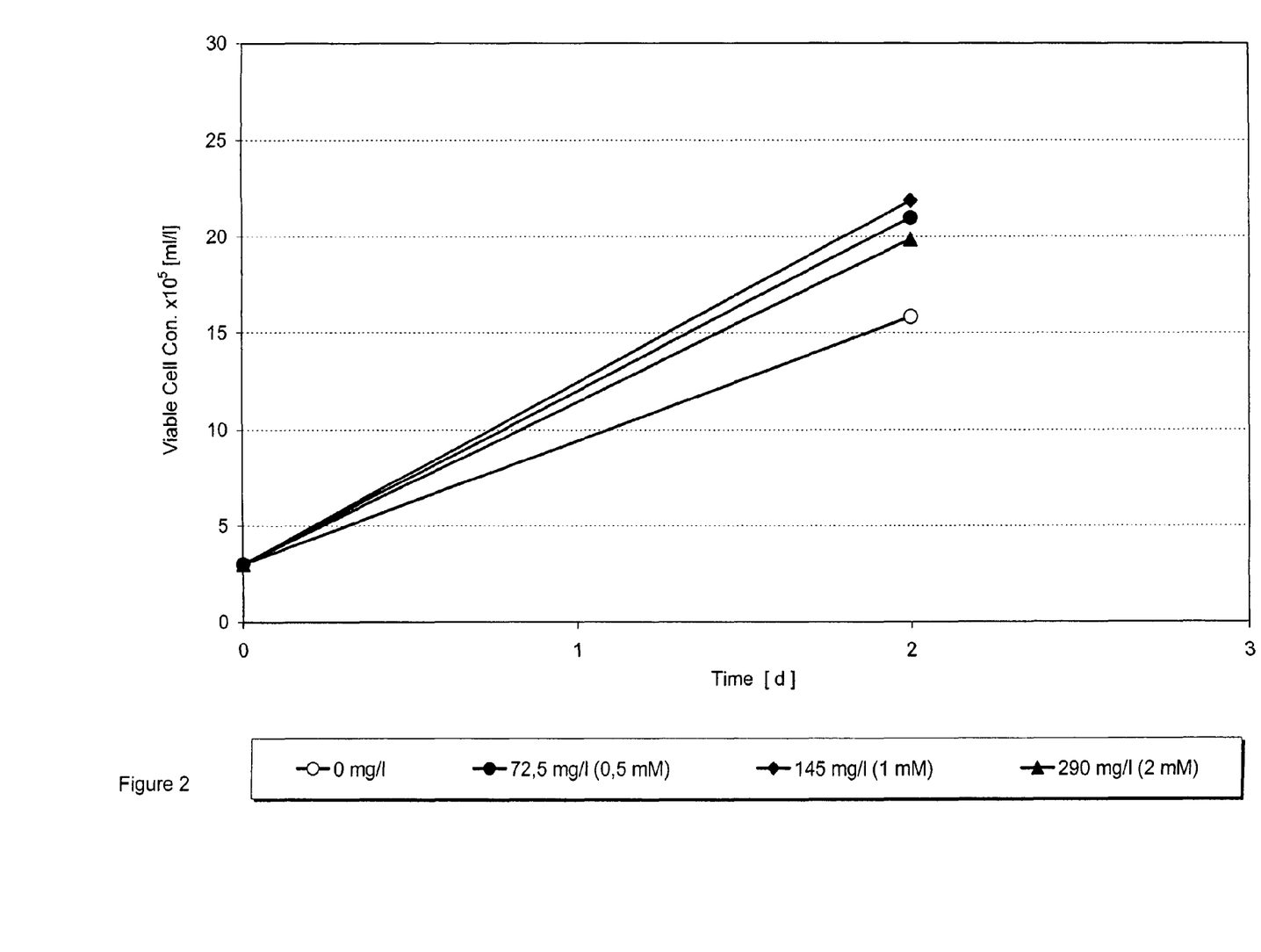
FIG. 2 demonstrates the use of spermidine as polyamine source in the presence of 100 mg/l iron (III) pyrophosphate in a batch process.

A cell culture medium is prepared with 100 mg/l iron (III) pyrophosphate hydrate (P6526) and without polyamine source. A stock solution of spermidine (S4139) is prepared. A corresponding amount of spermidine stock solution is pipetted into the culture medium to adjust the final concentration of spermidine, as is evident from the legend of FIG. 2. Then the so prepared culture media are inoculated with cells. The experiment is performed in batch modus. FIG. 2 demonstrates that cells reach a higher concentration in a batch process, if spermidine is available. To our surprise, the toxicity of spermidine is not visible at the tested high concentrations.

Example 3

Is Higher Spermine Concentration Needed in a High Cell Density Fed-Batch Process (FB117)?

Typically, the peak cell concentration in a fed batch process is higher than in a batch process. Therefore, the demand on nutrient concentrations is higher as compared to a batch process. Especially in a high cell density process, where the cell concentration exceeds $1\times10^7$/ml, more spermine and iron could be needed.

A cell culture medium is prepared with 100 mg/l iron (III) pyrophosphate hydrate (P6526) and without polyamine source. A stock solution of spermine (S4264) is prepared with a concentration of 40 g/l. A corresponding amount of stock solution is pipetted in the culture medium to adjust the final concentration of spermine, as is evident from the legend of FIG. 3. Then the so prepared culture media are inoculated with cells. The experiment is performed in fed-batch modus. All cultures were fed with the proprietary feeding medium, containing substrates for cell growth and viability, such as amino acids and glucose. The feeding medium is without polyamine and contains iron (III) pyrophosphate hydrate at a concentration of 800 mg/l.

Figure 3:
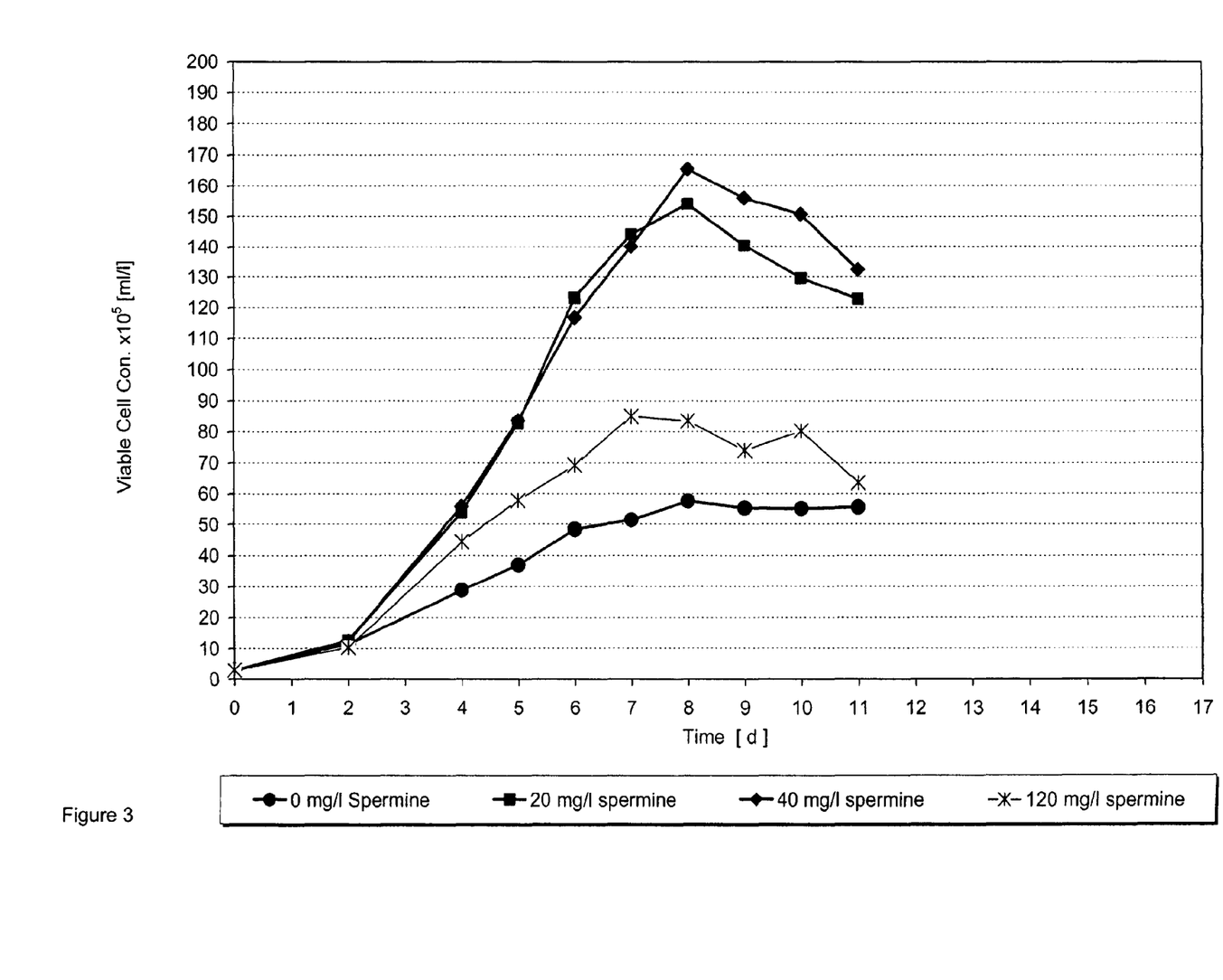
FIG. 3 demonstrates the effect of the spermine concentration in the presence of 100 mg/l iron (III) pyrophosphate in a high cell density fed-batch process.

FIG. 3 demonstrates that the cells grow better with increasing spermine concentration. The optimum concentration of spermine at the given iron concentration is in the example from 40 to 120 mg/l.

Example 4

Is Higher Iron Concentration Needed to Saturate High Spermine Concentration (SF57)?

Figure 4:
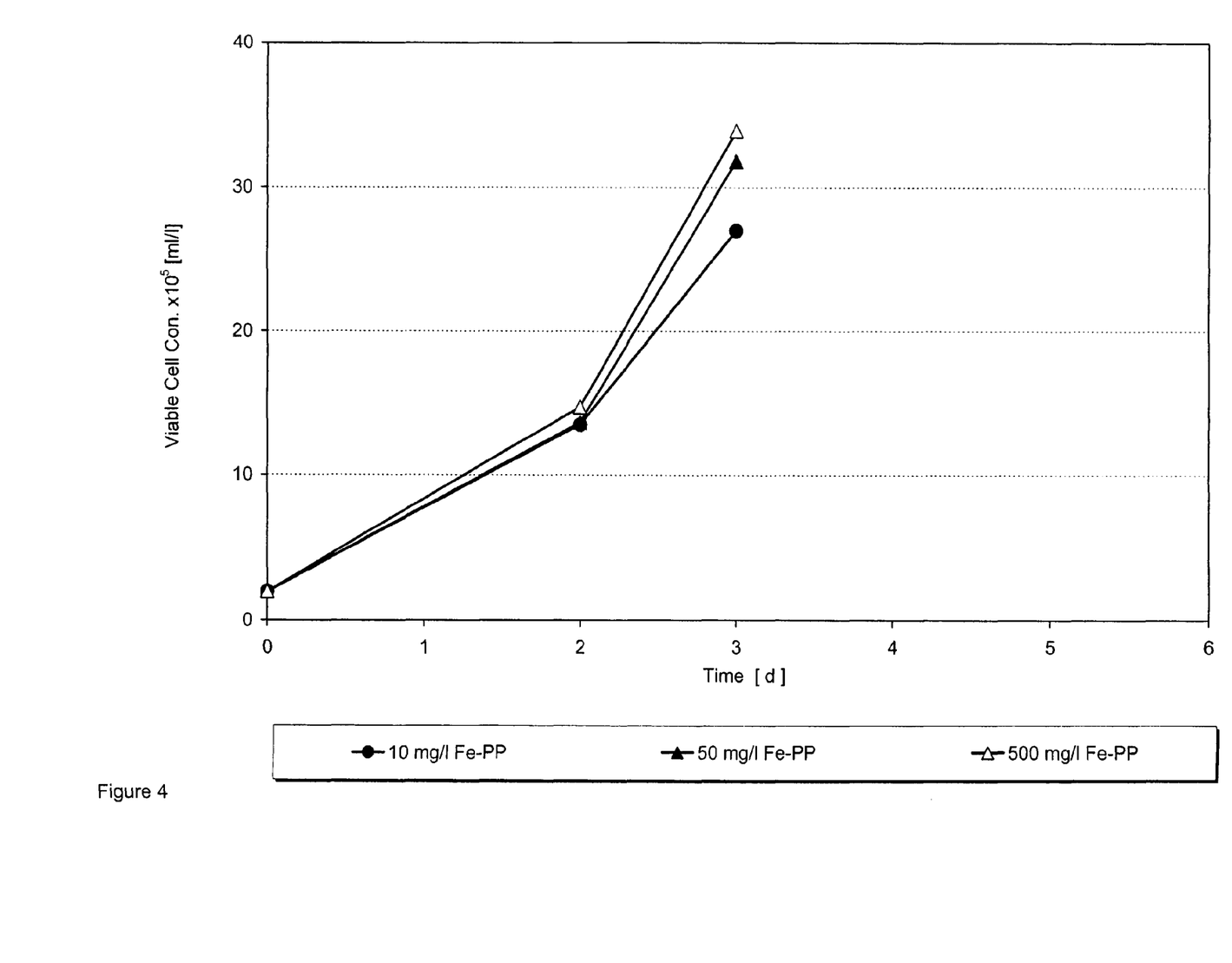
FIG. 4 demonstrates the effect of the iron concentration in the presence of 40 mg/l spermine in a batch process.

A spermine concentration of 40 mg/l was found to be good in example 3. A cell culture medium is prepared with a constant spermine concentration of 40 mg/l. Stock solutions of iron (III) pyrophosphate hydrate (P6526) are prepared with concentrations of 5 g/l and 50 g/l. Corresponding amounts of stock solutions are pipetted into the culture medium to adjust the final concentration of iron in the cultivation medium, as is evident from the legend of FIG. 4. Then the so prepared culture media are inoculated with cells. The experiment is performed in batch modus. FIG. 4 demonstrates that an extremely high iron concentration is tolerable to cells in the presence of spermine.

Example 5

Analysis of Spermine in Combination with Iron Nitrate in a Batch Process (SF107)

Figure 5:
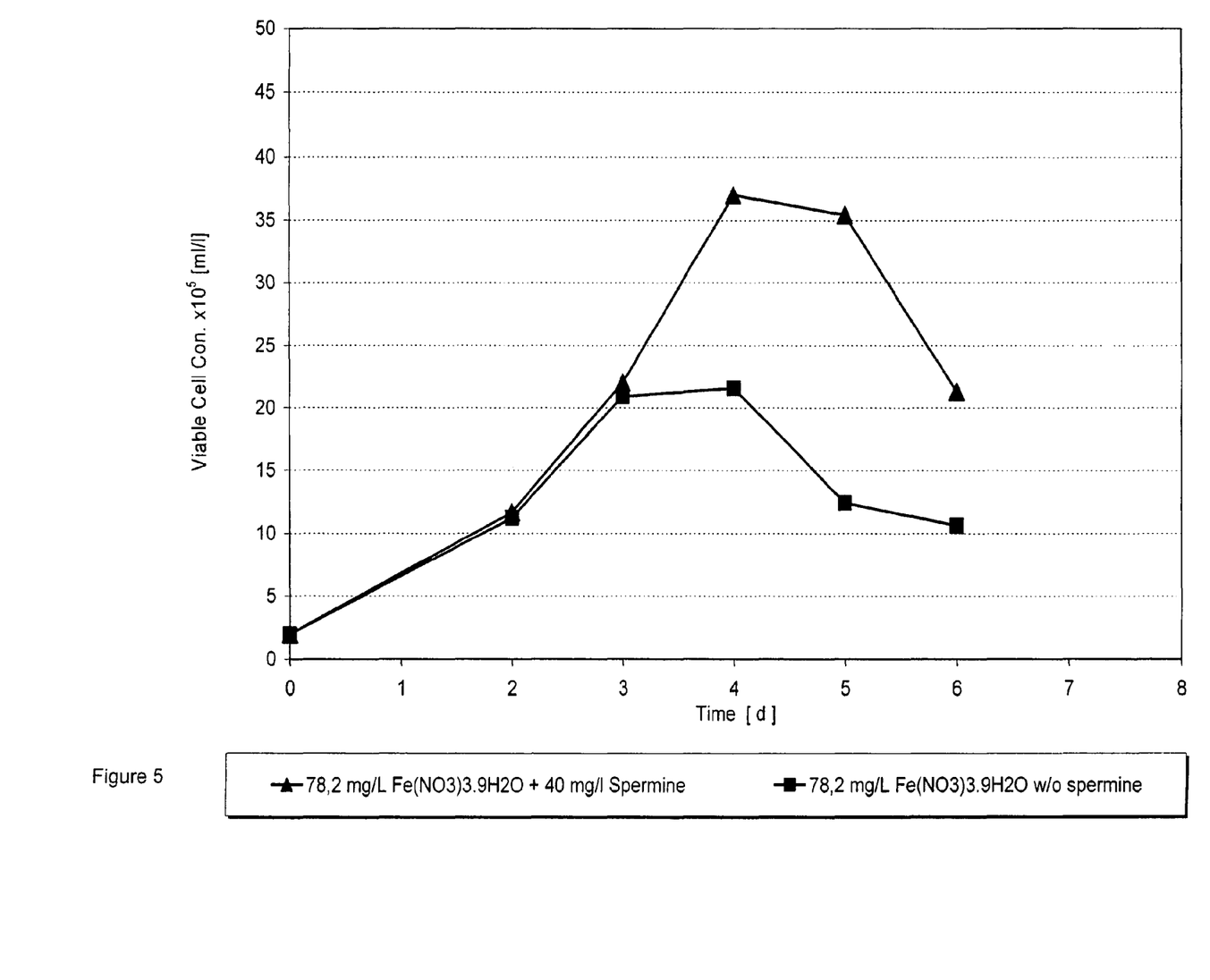
FIG. 5 demonstrates the effect of the iron source alone and in combination with spermine in a batch process.

This example demonstrates the synergistic effect of iron and spermine with an alternative iron source. A cell culture medium is prepared without iron and without polyamine source. Stock solutions of iron (III) nitrate nonahydrate (CAS Number: 7782-61-8) and spermine were prepared. A corresponding amount of stock solution is pipetted into the culture medium to adjust the final concentration of the test substances, as is evident from the legend of FIG. 5. Then the so prepared culture media are inoculated with cells. The experiment is performed in batch modus. FIG. 5 demonstrates that the cells reach higher concentrations in a batch process, if both spermine and iron are available at a high concentration, indicating the synergistic effects of both substances.

Example 6

Analysis of the spermine Concentration in Combination with Iron Citrate in Fed-Batch (FB188)

This experiment analyses the synergistic effect of spermine with iron (III) citrate in a high cell density fed-batch process. The iron source is iron (III) citrate (CAS number: 3522-50-7). A cell culture medium is prepared without iron and without polyamines.

Figure 6:
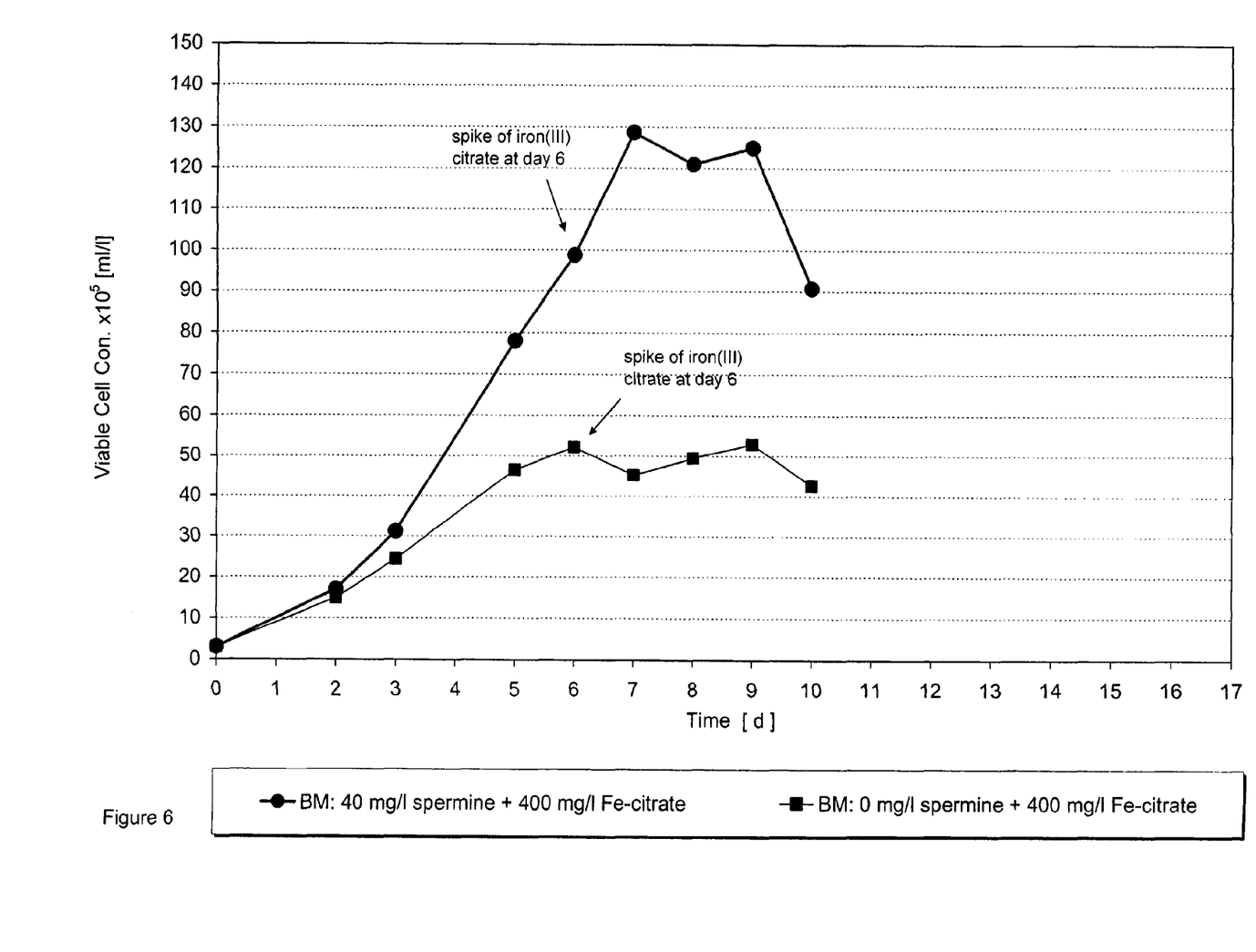
FIG. 6 demonstrates the effect of the iron source alone and in combination with spermine in a high cell density fed-batch process.

A stock solution of spermine is prepared at 40 g/l (S4264). A stock solution of iron (III) citrate is prepared at 50 g/l. Corresponding amounts of the stock solutions are pipetted into the culture medium to adjust the desired final concentration of spermine and iron (III) citrate in the culture medium, as is evident from the legend of FIG. 6. The feed medium was free of iron and free of spermine. The cells were transferred into the prepared media. The experiment is performed in fed-batch modus. All cultures were fed with a feeding medium containing substrates for cell growth and viability, such as amino acids and glucose. All cultures were further supplemented with iron (III) citrate at day 6 to a final concentration of 400 mg/l. FIG. 6 demonstrates that for optimal cell growth spermine and iron both are required. In addition, a significantly high spermine and iron concentration is needed, Such a high spermine and iron concentration is particularly required in a high cell density fed-batch process, in which the cell concentration exceeds $1 \times 10^7$/ml.

Example 7

Test of Spermine in Combination with Different Iron Citrate Concentration in Fed-Batch (FB171-3)

The goal was to test if the positive effect of polyamines is visible on cell growth with another iron source as well. In this experiment iron citrate was tested in a fed-batch process with and without spermine. A cell culture medium is prepared without iron and without polyamines. A stock solution of spermine is prepared at 40 g/l (S4264). A stock solution of iron (III) citrate is prepared at 50 g/l (CAS number: 3522-50-7).

Figure 7:
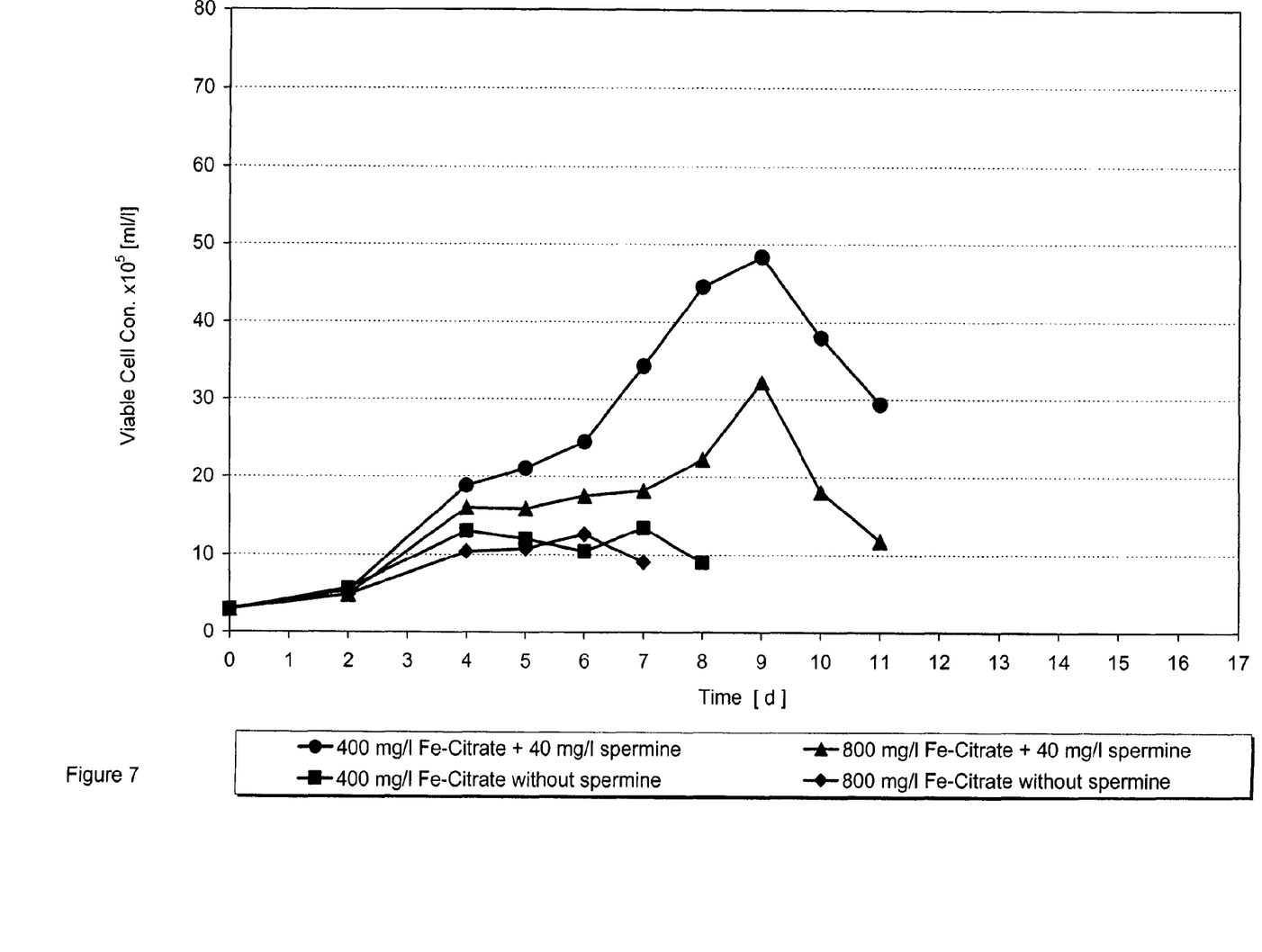
FIG. 7 demonstrates the positive effect of the spermine concentration with iron (III) citrate.

Corresponding amounts of the stock solutions are pipetted into the culture medium to adjust the desired final concentration of spermine and iron (III) citrate, as is evident from the legend of FIG. 7. The inoculum cells were cultured three days in a polyamine and iron free medium to deplete the intracellular iron and polyamine pool. Then the so conditioned cells are used as inoculum. The experiment is performed in fed-batch modus. All cultures were fed with a feeding medium containing substrates for cell growth and viability, such as amino acids and glucose. The feeding medium is without polyamines and contains iron (III) citrate at a concentration of 3200 mg/l. FIG. 7 demonstrates that the positive effect of spermine is also seen with other iron sources. Furthermore, cells tolerate very high iron concentration up to 800 mg/l in the presence of spermine.

Example 8

Test of Spermine in Combination with Iron (III) Phosphate in Fed-Batch (171-2)

The goal was to test if the positive effect of the previously analysed polyamine concentration on cell growth is visible with another iron source as well. In this experiment iron (III) phosphate (F1523) was tested with and without spermine. A cell culture medium is prepared without iron and without polyamines. A stock solution of spermine is prepared at 40 g/l (S4264). A stock solution of iron (III) phosphate is prepared at 50 g/l.

Figure 8:
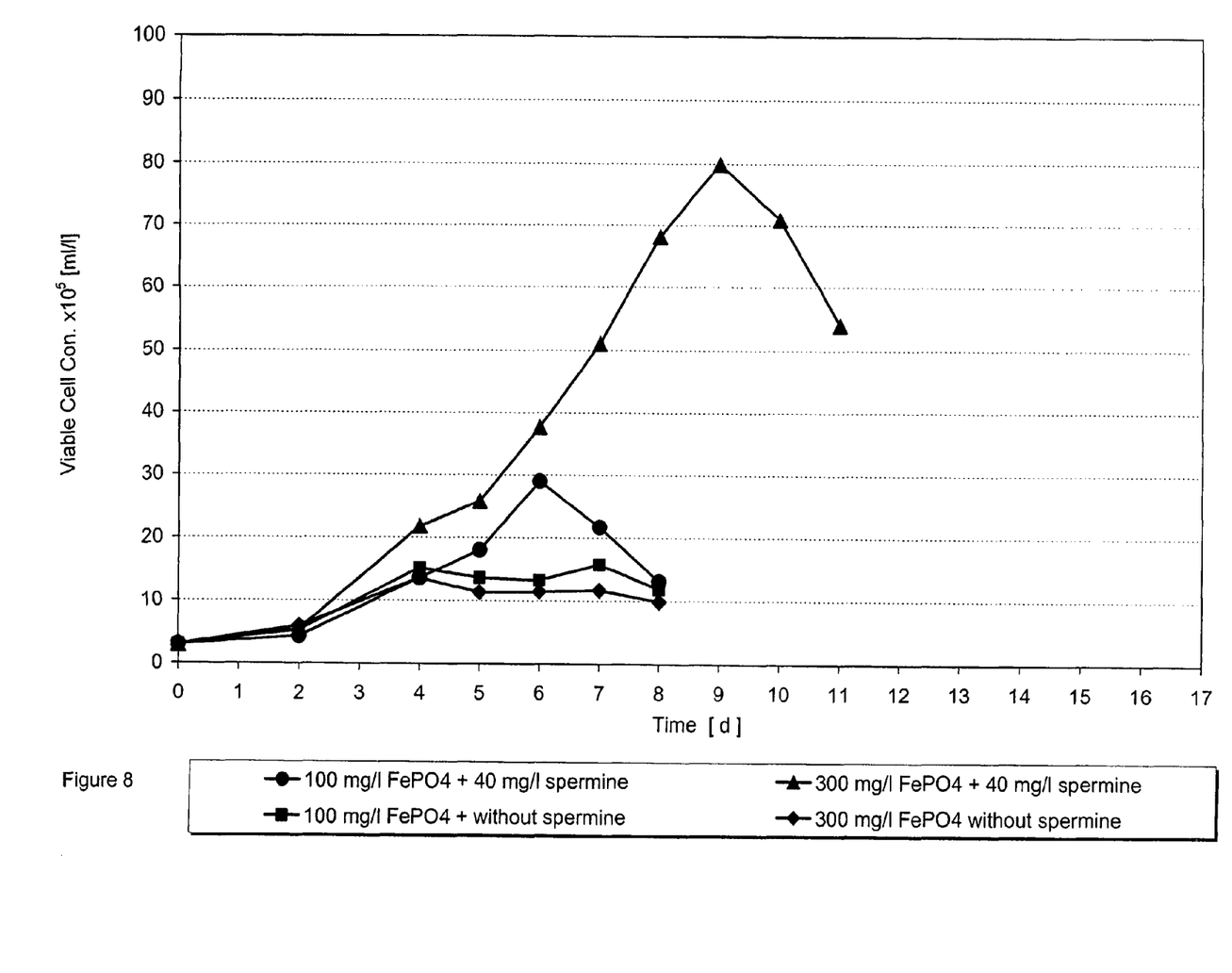
FIG. 8 demonstrates the effect of the spermine concentration with iron (III) phosphate.

Corresponding amounts of stock solutions are pipetted in the culture medium to adjust the desired final concentration of spermine and iron (III) phosphate, as is evident from the legend of FIG. 8. Then the so prepared culture media are inoculated with cells. The experiment is performed in fed-batch modus. All cultures were fed with a feeding medium containing substrates for cell growth and viability, such as amino acids and glucose. The feeding medium is without polyamines and contains iron (III) phosphate at a concentration of 800 mg/l.

FIG. 8 demonstrates that the positive effect of spermine is also seen with iron (III) phosphate. It is surprising to see that such a high iron concentration is not toxic to the cells in the presence of spermine, rather it promotes cell growth.

Example 9

Test of Spermine in Combination with Iron Dextran in Fed-Batch (174-1)

The goal was to test if the positive effect of the previously analysed polyamine concentration on cell growth is visible with another iron source as well. In this experiment iron dextran (D8517) was tested. A cell culture medium is prepared with spermine concentration of 40 mg/l. The medium was without iron source.

Figure 9:
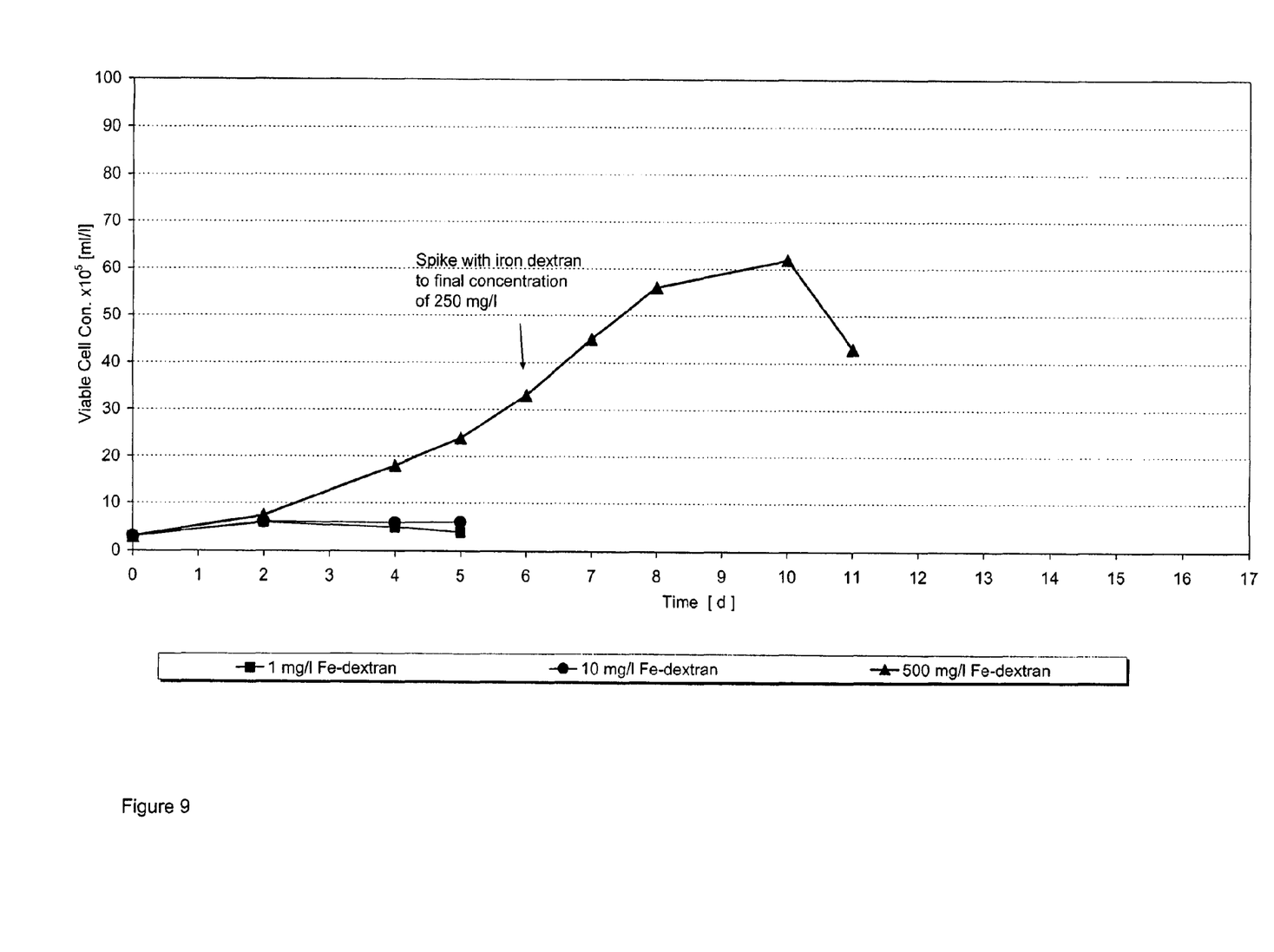
FIG. 9 demonstrates the effect of the spermine concentration with iron-dextran.

A solution of iron-dextran with a concentration of 100 g/l was purchased from Sigma. Before start of the experiment, the cells were cultured for two days in a medium without iron source. In this way, the intracellular iron pool was depleted. However, a previous starvation of cells of iron is not a requirement for the functionality of spermine and iron-dextran. The cells were starved of iron. Such cells were transferred into the prepared media as described above. The experiment is performed in fed-batch modus. Feed medium was without spermine and without iron. All cultures were fed with a feeding medium, containing substrates for cell growth and viability, such as amino acids and glucose. The growing culture was fed further with iron dextran at day 6 to a final iron dextran concentration of 250 mg/l. FIG. 9 demonstrates that for optimal cell growth a very high iron dextran concentration is needed in the presence of spermine. It is surprising to see that such a high iron concentration is not toxic for cells and it promotes cell growth.

What is claimed is:

1. A cell culture medium wherein mammalian cells are cultured, said medium containing at least one polyamine at a concentration of from 30 mg/l to 120 mg/l and at least one iron source at a concentration of from 50 mg/l to 900 mg/l, wherein the polyamine is one or more of the compounds or salts thereof or hydrated or dehydrated forms thereof selected from: spermidine, spermine, norspermine, norspermidine, homospermine and homospermidine.

2. The cell culture medium according to claim 1, wherein the iron source contains at least one of Fe (II) ions and Fe (III) ions.

3. The cell culture medium according to claim 1, wherein the iron source is one or more of the compounds or salts thereof or hydrated or dehydrated forms thereof selected from: iron (III) phosphate, iron (III) pyrophosphate, iron (III) nitrate, iron (II) sulphate, iron (III) chloride, iron (II) lactate, iron (III) citrate, ammonium iron (III) citrate, iron-dextran and ethylenediaminetetraacetic acid ferric sodium salt.

4. The cell culture medium according to claim 1, wherein the polyamine is spermine.

5. The culture medium according to claim 1, which contains at least one compound selected from: aurin tricarboxylic acid (ATA), dichloro acetic acid (DCA), succinic acid, salts thereof and derivatives thereof.

6. The cell culture medium according to claim 1, which is serum free.

7. The cell culture medium according to claim 1, which is free of glutamine.

8. The cell culture medium according to claim 1, which is protein free.

9. The cell culture medium according to claim 1, which is provided in form of a kit.

10. A process for preparing a cell culture medium wherein mammalian cells are cultured according to claim 1, said cell culture medium containing at least one polyamine at a concentration of from 30 mg/L to 120 mg/L and at least one iron source at a concentration of from 50 mg/L to 900mg/L, wherein the polyamine is one or more selected from the compounds or salts thereof or hydrated or dehydrated forms thereof selected from: spermidine, spermine, norspermine, norspermidine, homospermine, and homospermidine, wherein a culture additive is added to a liquid medium, wherein the culture additive contains at least one polyamine at a concentration of at least 30 mg/1 and at least one iron source at a concentration of at least 50 mg/1, wherein the polyamine is one or more of the compounds or salts thereof or hydrated or dehydrated forms thereof selected from: spermidine, spermine, norspermine, norspermidine, homospermine, and homospermidine.

11. The process according to claim 10, wherein the liquid culture medium is a conventional culture medium containing an aqueous solvent, a carbon source and a nitrogen source.

12. A cell culture medium prepared according to the process of claim 10.

13. A process for culturing cells in a culture medium, wherein
a) the cells and the culture medium according to claim 1 are provided, and
b) the cells are cultivated in said culture medium under conditions appropriate for maintenance of said cells in said culture.

14. The process according to claim 13, wherein the process comprises producing at least one protein from said cells.

15. A process for culturing cells in a culture medium, wherein
a) the cells and a culture medium are provided; and b) the cells are cultivated in said culture medium under conditions appropriate for maintenance of said cells in said culture medium, and c) at least one polyamine source is added to a concentration of 30 mg/L to 120 mg/L and at least one iron source is added to a concentration of from 50 mg/L to 900mg/L, wherein the polyamine is one or more selected from the compounds or salts thereof or hydrated or dehydrated forms thereof selected from: spermidine, spermine, norspermine, norspermidine, homospermine, and homospermidine,
wherein the polyamine source and iron source are added to the culture medium before inoculating said culture medium with cells or after inoculating said first culture medium with cells or during the cultivation.

* * * * *

UNITED STATES PATENT AND TRADEMARK OFFICE
CERTIFICATE OF CORRECTION

PATENT NO.        : 8,637,312 B2                                             Page 1 of 1
APPLICATION NO. : 12/811747
DATED             : January 28, 2014
INVENTOR(S)       : Krüger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 517 days.

Signed and Sealed this
Twenty-second Day of September, 2015

Michelle K. Lee
*Director of the United States Patent and Trademark Office*